(12) United States Patent
Wada et al.

(10) Patent No.: US 10,265,346 B2
(45) Date of Patent: Apr. 23, 2019

(54) TREHALOSE-CONTAINING MAMMALIAN CELL SUSPENSION FOR PREVENTION OF PULMONARY EMBOLISM FORMATION

(71) Applicant: OTSUKA PHARMACEUTICAL FACTORY, INC., Tokushima (JP)

(72) Inventors: Tamaki Wada, Tokushima (JP); Masako Doi, Tokushima (JP); Takeshi Kikuchi, Tokushima (JP); Eiji Kobayashi, Tokushima (JP)

(73) Assignee: OTSUKA PHARMACEUTICAL FACTORY, INC., Tokushima (JP)

( * ) Notice: Subject to any disclaimer, the term of this patent is extended or adjusted under 35 U.S.C. 154(b) by 545 days.

(21) Appl. No.: 14/398,321

(22) PCT Filed: May 2, 2013

(86) PCT No.: PCT/JP2013/002925
§ 371 (c)(1),
(2) Date: Oct. 31, 2014

(87) PCT Pub. No.: WO2013/168403
PCT Pub. Date: Nov. 14, 2013

(65) Prior Publication Data
US 2015/0118196 A1    Apr. 30, 2015

(30) Foreign Application Priority Data

May 8, 2012  (JP) ................................. 2012-106866

(51) Int. Cl.
*A61K 35/28* (2015.01)
*A61K 35/545* (2015.01)
*A61K 31/7016* (2006.01)

(52) U.S. Cl.
CPC ........ *A61K 35/545* (2013.01); *A61K 31/7016* (2013.01); *A61K 35/28* (2013.01)

(58) Field of Classification Search
None
See application file for complete search history.

(56) References Cited

U.S. PATENT DOCUMENTS

| | | | |
|---|---|---|---|
| 2001/0055583 A1 | 12/2001 | Roser et al. | |
| 2005/0163750 A1* | 7/2005 | Roser .................. | A61K 9/0019 424/85.2 |
| 2010/0047213 A1 | 2/2010 | Zeitlin et al. | |
| 2013/0260461 A1 | 10/2013 | Kobayashi et al. | |

FOREIGN PATENT DOCUMENTS

| | | |
|---|---|---|
| CA | 2 355 879 A1 | 6/2000 |
| EP | 0 580 444 A1 | 1/1994 |
| JP | 10-500990 A | 1/1998 |
| JP | 3253131 B2 | 11/2001 |
| JP | 2002-532567 A | 10/2002 |
| JP | 2012-500021 A | 1/2012 |
| JP | 2012-115253 A | 6/2012 |
| WO | 95/33488 A1 | 12/1995 |
| WO | 00/37112 A1 | 6/2000 |
| WO | 2007/043698 A1 | 4/2007 |
| WO | WO 2010048628 A1 * | 4/2010 ........... A61K 31/198 |

OTHER PUBLICATIONS

European Search Report issued with respect to application No. 13788054.8, dated Sep. 23, 2015.
Dario Furlani et al., "Is the intravascular administration of mesenchymal stem cells safe? Mesenchymal stem cells and intravital microscopy", Macrovascular Research 77, 2009, pp. 370-376.
Chun Fang Wu et al., "Improved cryopreservation of human embryonic stem cells with trehalose", Reproductive BioMedicine Online, vol. 11, No. 6, 2005, pp. 733-739.
Shao-zhi Zhang et al., "Preliminary study on the freeze-drying of human bone marrow-derived mesenchymal stem cells", Journal of Zhejiang University—Science B (Biomediciane and Biotechnology), 2010, 11, pp. 889-894.
Eduard Bathe et al., "B-Catenin and TCF Mediate Cell Positioning in the Intestinal Epithelium by Controlling the Expression of EphB/EphrinB", Cell Press, Oct. 18, 2002, pp. 251-263, vol. 111.
International preliminary report on patentability of application No. PCT/JP2013/002925, dated Nov. 11, 2014.
Chen Fengshi et al., "Development of New Organ Preservation Solutions in Kyoto University", Department of Thoracic Surgery, Graduate School of Medicine, Kyoto University, 2004, pp. 1107-1114, vol. 45, No. 6.
Hidemi Hattori et al., "Preservation of stem cells during cold storage", Divison of Biomedical Engineering, Research Institue, National Defense Medical College, Department of Medical Engineering, May 2004, p. 538, vol. 42.

(Continued)

*Primary Examiner* — Emily A Cordas
(74) *Attorney, Agent, or Firm* — Greenblum & Bernstein, P.L.C.

(57) ABSTRACT

A mammalian cell suspension prevents pulmonary embolism formation during administration of mammalian cells, such as mammalian stem cells, through a blood vessel, and a preventive agent against pulmonary embolism formation during administration of mammalian cells through a blood vessel. suspending mammalian cells, such as mammalian stem cells, are suspended in a physiological aqueous solution containing trehalose or its derivative, or a salt thereof as an active ingredient to prepare a mammalian cell suspension for preventing pulmonary embolism formation during administration of the mammalian cells through a blood vessel, including the mammalian cells and trehalose or its derivative, or a salt thereof as active ingredients. Examples of the mammalian cells can include pancreatic islet cells, dendritic cells, natural killer cells, alpha/beta T cells, gamma/delta T cells, and cytotoxic T lymphocytes in addition to mammalian stem cells. Preferred mammalian stem cells can include mammalian mesenchymal stem cells and mammalian pluripotent stem cells.

12 Claims, 1 Drawing Sheet

(56) References Cited

OTHER PUBLICATIONS

Eduard Batlle et al., "B-Catenin and TCF Mediate Cell Positioning in the Intestinal Epithelium by Controlling the Expression of EphB/EphrinB", Cell Press, Oct. 18, 2002, PP. 251-263, vol. 111.
Sean J. Morrison et al., "Prospective Identification, Isolation by Flow Cytometry, and In Vivo Self-Renewal of Multipotent Mammalian Neural Crest Stem Cells", Cell Press, Mar. 5, 1999, pp. 737-749, vol. 96.
Fred H. Gage, "Mammalian Neural Steam Cells", Stem Cell research and Ethics, Feb. 25, 2000, pp. 1433-1438.
Search report from PCT/JP2013/002925, dated Jul. 23, 2013.

* cited by examiner

[Figure 1]
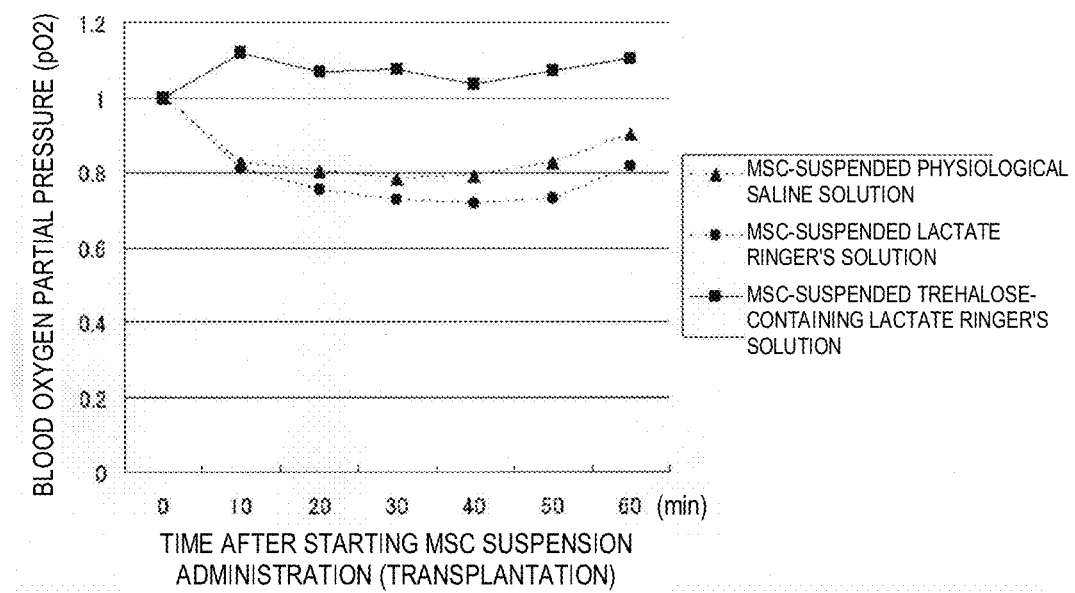
[Figure 2]
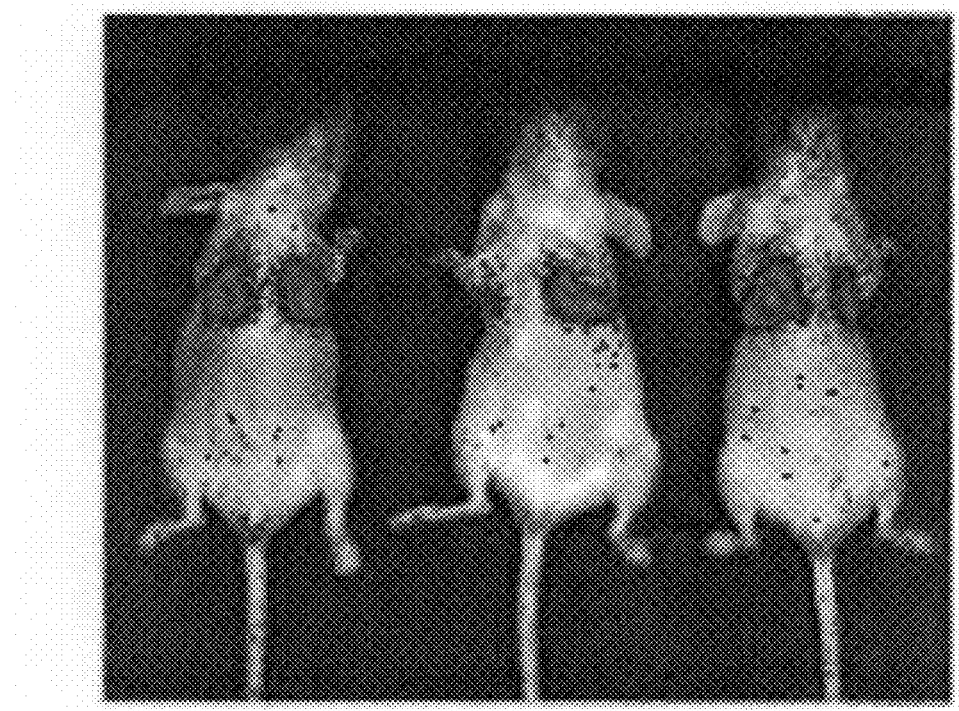

TREHALOSE-CONTAINING MAMMALIAN CELL SUSPENSION FOR PREVENTION OF PULMONARY EMBOLISM FORMATION

TECHNICAL FIELD

The present invention relates to a mammalian cell suspension for preventing pulmonary embolism formation during administration of mammalian cells through a blood vessel, comprising mammalian cells and trehalose or its derivative, or a salt thereof, a preventive agent against pulmonary embolism formation during administration of mammalian cells through a blood vessel, comprising trehalose or its derivative, or a salt thereof as an active ingredient, and the like.

BACKGROUND ART

In recent years, rapid progress of stem cell studies has increased momentum toward regenerative medicine, and the knowledge and understanding thereof have been widespread not only in researchers but also in the public. Regenerative medicine using stem cells is medicine intended for reestablishing the function of cells and tissues damaged by various diseases by utilizing the self-renewal potential and pluripotency of stem cells or factors secreted by stem cells. Bone-marrow transplantation in patients having intractable hematological diseases such as leukemia and aplastic anemia results in the engraftment of hematopoietic stem cells in the body of these patients, which permits the maintenance of hematopoietic capacity over almost their entire life. Recently, many researchers have aimed at clinical application using stem cells other than hematopoietic stem cells, have identified stem cells in the central nerves, peripheral nerves, bone marrow, small intestine, and the like, and stem cell transplantation treatment has been started for traumatic disease and tissue degeneration disease (Non-patent Documents 1 to 3).

For efficient transplantation of mammalian stem cells into a target damaged site (an affected site), it is considered to be important to optimize a method (route) for transplantation of stem cells. To date, mainly 4 types of methods, i.e., a stereotactic (direct) transplantation method, an intrathecal (intracerebrospinal) transplantation method, an intravenous transplantation method, and an intraarterial transplantation method, are known as transplantation methods for stem cells. Among these, the stereotactic transplantation method is a method which involves transferring stem cells directly into an affected site. Use of the stereotactic transplantation method can increase the number of engrafting donor's stem cells because of direct administration into an affected site, thus decreasing the number of administered stem cells, although the method is slightly invasive. The intrathecal transplantation method is a method which involves intrathecally transferring stem cells by ventriculopuncture. The intrathecal transplantation method is a method which has been studied mainly for the treatment of brain diseases such as cerebral infarction, cerebral contusion, and spinal cord damage; however, it still leaves many problems in the clinical application thereof, such as the potential risk of the ventriculopuncture causing new cerebral damage.

The intravenous transplantation method and the intraarterial transplantation method are methods for transferring cells such as stem cells intravenously and intraarterially, respectively (methods for administration through the blood vessels). Use of the method for administration through a blood vessel is less invasive and can systemically circulate cells such as stem cells and factors secreted by cells such as stem cells, although it decreases the number of engrafting donor's liver cells compared to the use of the stereotactic transplantation method. At present, a method involving intravenously transplanting mesenchymal stem cells (MSC) for cerebral infarction disease, a method involving intravenously transplanting mononuclear cells for cerebral infarction disease, a method involving intravenously transplanting pancreatic islet cells into type I diabetes patients, and the like are known as clinically performed methods for administration through a blood vessel.

As a risk when cells such as stem cells are transplanted using the method for administration through a blood vessel, it has been pointed out that intraarterially or intravenously administered cells get clogged in capillary blood vessels of the pulmonary artery (pulmonary embolism) in passing through the lung, resulting in reduced pulmonary and cardiac function (pulmonary embolic disease) and, in some cases, posing a risk of leading to death. To prevent pulmonary embolism formation and pulmonary embolic disease, stem cells are transplanted in clinical sites while monitoring the partial pressure of oxygen in the peripheral blood during the administration of stem cells by a pulse oximeter.

Meanwhile, trehalose is a type of disaccharide formed by the 1,1-glycosidic linkage of two glucose molecules. Trehalose is used in various foods and cosmetics because it presents a sweet taste and has a high water retaining capacity. Trehalose is also used as an active ingredient of an organ-protecting solution in transplanting the organ because it has the properties of stabilizing cell membrane and suppressing cell damage. Excellent organ preservation solutions containing trehalose have been developed, such as ET-Kyoto solution and New ET-Kyoto solution (Patent Documents 1 and 2 and Non-patent Document 4). However, it has been unclear whether the risk of pulmonary embolism formation by cells is reduced or not or pulmonary embolic disease is prevented or not when cells such as stem cells are suspended in a trehalose-containing solution and the cell suspension is administered through a blood vessel.

PRIOR ART DOCUMENTS

Patent Documents

Patent Document 1: Japanese Patent No. 3253131
Patent Document 2: International Publication No. WO2007/043698

Non-Patent Documents

Non-patent Document 1: Gage, F. H. Science 287: 1433-1438 (2000)
Non-patent Document 2: Morrison, S. J. et al., Cell 96: 737-749 (1999)
Non-patent Document 3: Batle, E. et al., Cell 111: 251-263 (2002)
Non-patent Document 4: Chem, F. et al., Yonsei Med. J. 45: 1107-1114 (2004)

SUMMARY OF THE INVENTION

Object to be Solved by the Invention

An object of the present invention is to provide a mammalian cell suspension capable of preventing pulmonary embolism formation during administration of the mammalian cells, such as mammalian stem cells, through a blood vessel, and a preventive agent against pulmonary embolism formation during administration of mammalian cells through a blood vessel.

Means to Solve the Object

The present inventors found that the suspension of mammalian stem cells in a trehalose-containing solution suppressed the aggregation of the mammalian stem cells and suppressed a reduction in survival rate (Japanese Patent Application No. 2010-251273). Possible causes of pulmonary embolism formation by stem cell transplantation include that cell masses in each of which the stem cells are aggregated clog capillary blood vessels of the pulmonary artery; however, only the simple inhibition of the cell aggregation has also been well thought not to inhibit the pulmonary embolism formation by stem cells, because whereas the size of stem cells, for example, mesenchymal stem cells (MSC), is 10 to 50 μm, the inner diameter of capillary blood vessels of pulmonary artery is 10 μm, that is, the size of MSC is larger than that of capillary blood vessels of the pulmonary artery. The present inventors have found that when MSC is suspended in a trehalose-containing lactate Ringer's solution and the MSC-suspended trehalose-containing lactate Ringer's solution is intravenously administered to rats, no reduction in the blood oxygen partial pressure is observed during or after administration and the accumulation of MSC populations in the lung is decreased compared to that for the use of a trehalose-free lactate Ringer's solution or a physiological saline solution as a control as a suspension, thereby accomplishing the present invention.

Thus, the present invention relates to: (1) a mammalian cell suspension for preventing pulmonary embolism formation during administration of mammalian cells through a blood vessel, comprising mammalian cells and trehalose or its derivative, or a salt thereof; (2) the mammalian cell suspension according to (1) above, wherein the mammalian cells are mammalian stem cells; β) the mammalian cell suspension according to (2) above, wherein the mammalian stem cells are mammalian mesenchymal stem cells or mammalian pluripotent stem cells; (4) the mammalian cell suspension according to any one of (1) to β) above, wherein the mammalian cells comprise the mammalian cells in a single cell state; and (5) the mammalian cell suspension according to any one of (1) to (4) above, wherein trehalose or its derivative, or a salt thereof has a concentration ranging from 0.1 to 20%.

The present invention also relates to: (6) a preventive agent against pulmonary embolism formation during administration of mammalian cells through a blood vessel, comprising trehalose or its derivative, or a salt thereof as an active ingredient; (7) the preventive agent according to (6) above, wherein the mammalian cells are mammalian stem cells; and (8) the preventive agent according to (7) above, wherein the mammalian stem cells are mammalian mesenchymal stem cells or mammalian pluripotent stem cells.

The present invention further relates to: (9) use of trehalose or its derivative, or a salt thereof in the preparation of a preventive agent against pulmonary embolism formation during administration of mammalian cells through a blood vessel; and (10) the use according to (9) above, wherein the mammalian cells are mammalian stem cells.

Effect of the Invention

According to the present invention, the risk of forming pulmonary embolism during administration of mammalian cells, such as mammalian stem cells, through a blood vessel can be decreased and the risk of developing pulmonary embolic disease can be reduced.

BRIEF DESCRIPTION OF DRAWINGS

FIG. 1 is a graph showing the results of measuring blood oxygen partial pressure ($pO_2$) in rats to which was administered each of 3 types of MSC suspensions (MSC-suspended physiological saline solution [ . . . ▲ . . . ], MSC-suspended lactate Ringer's solution [ . . . ● . . . ], and MSC-suspended trehalose-containing lactate Ringer's solution [-■-]). The vertical axis represents blood oxygen partial pressure. The blood oxygen partial pressure is expressed as a relative value when that (0 minute) before MSC suspension administration is assumed as 1. The horizontal axis represents time after the start of MSC suspension administration.

FIG. 2 is a photograph showing the results of image analysis of the biodistribution of MSC in rats to which was administered each of 3 types of MSC suspensions (MSC-suspended physiological saline solution, MSC-suspended lactate Ringer's solution, and MSC-suspended trehalose-containing lactate Ringer's solution) (the left, middle, and right, respectively in the figure).

MODE OF CARRYING OUT THE INVENTION

The mammalian cell suspension for preventing pulmonary embolism formation during administration of mammalian cells, such as mammalian stem cells, through a blood vessel according to the present invention is not particularly limited provided that it is a suspension comprising mammalian cells, such as mammalian stem cells, and trehalose or its derivative, or a salt thereof (hereinafter referred to as a trehalose). The preventive agent against pulmonary embolism formation during administration of mammalian cells, such as mammalian stem cells, through a blood vessel according to the present invention is not particularly limited provided that it is a composition comprising a trehalose as an active ingredient. Examples of the mammal can include rodents such as mice, rats, hamsters, and guinea pigs, lagomorphs such as rabbits, ungulates such as pigs, cows, goats, horses, and sheep, Carnivora such as dogs and cats, and primates such as humans, monkeys, rhesus monkey, cynomolgus monkey, marmosets, orangutans, and chimpanzees; among others, mice, pigs, and humans can be preferably exemplified. Examples of the mammalian cells can include mammalian pancreatic islet cells intravenously administered to patients with type I diabetes, and mammalian dendritic cells, natural killer cells, alpha/beta (αβ) T cells, gamma/delta (γδ) T cells, and cytotoxic T lymphocytes (CTL) intravenously administered to cancer patients in addition to mammalian stem cells administered through a blood vessel for regenerative medicine or the like.

The "stem cell" means an immature cell having self-renewal potential and differentiation/proliferation potential. Stem cells include subpopulations, such as pluripotent stem cells, multipotent stem cells, and unipotent stem cells, according to differentiation ability. The pluripotent stem cell means a cell which, as such, cannot become an individual organism but has a capability of differentiating into all tissues or cells constituting a living body. The multipotent stem cell means a cell having a capability of differentiating into a plurality of, but not all, types of tissues or cells. The unipotent stem cell means a cell having a capability of differentiating into a particular tissue or cell.

Examples of the pluripotent stem cell include an embryonic stem cell (ES cell), an EG cell, and an iPS cell. ES cells can be produced by culturing an inner cell mass on feeder cells or in a medium containing LIF. The method for producing ES cells is described, for example, in WO96/22362, WO02/101057, U.S. Pat. Nos. 5,843,780, 6,200,806, and 6,280,718. EG cells can be produced by culturing primordial germ cells in a medium containing mSCF, LIF, and bFGF (Cell, 70: 841-847, 1992). iPS cells can be produced by introducing reprogramming factors such as Oct3/4, Sox2, and Klf4 (and optionally further c-Myc or n-Myc) into somatic cells (for example, fibroblasts or skin cells) (Cell, 126: p. 663-676, 2006; Nature, 448: p. 313-317, 2007; Nat. Biotechnol, 26; p. 101-106, 2008; Cell 131: p. 861-872, 2007; Science, 318: p. 1917-1920, 2007; Cell Stem Cells 1: p. 55-70, 2007; Nat. Biotechnol, 25: p. 1177-1181, 2007; Nature, 448: p. 318-324, 2007; Cell Stem Cells 2: p. 10-12, 2008; Nature 451: p. 141-146, 2008; Science, 318: p. 1917-1920, 2007). Stem cells established by culturing early embryos prepared by transplanting the nucleus of somatic cells are also preferable as pluripotent stem cells (Nature, 385, 810 (1997); Science, 280, 1256 (1998); Nature Biotechnology, 17, 456 (1999); Nature, 394, 369 (1998); Nature Genetics, 22, 127 (1999); Proc. Natl. Acad. Sci. USA, 96, 14984 (1999)), and Rideout III et al., (Nature Genetics, 24, 109 (2000)).

Examples of the multipotent stem cell include somatic stem cells including a mesenchymal stem cell capable of differentiating into cells such as an adipocyte, an osteocyte, a chondrocyte, and an adipocyte, a hematopoietic progenitor capable of differentiating into blood cells such as a leucocyte, an erythrocyte, and a platelet, a neural stem cell capable of differentiating into cells such as a neuron, an astrocyte, and an oligodendrocyte, a myeloid stem cell, and a germ stem cell. The multipotent stem cell is preferably a mesenchymal stem cell. The mesenchymal stem cell means a stem cell capable of differentiating into all or some of an osteoblast, a chondroblast, and a lipoblast. Functional stem cells can be isolated from a living body by methods known per se.

For example, the mesenchymal stem cells can be collected from the mammalian bone marrow, fat tissue, peripheral blood, cord blood, and the like by well-known general methods. For example, human mesenchymal stem cells can be isolated by culturing and subculturing hematopoietic stem cells or the like after bone marrow puncture (Journal of Autoimmunity, 30 (2008) 163-171). Multipotent stem cells can also be obtained by culturing the above-described pluripotent stem cells under suitable induction conditions.

The cells, such as stem cells, contained in the mammalian cell suspension of the present invention cells can be exemplified by adherent cells. Although adherent cells are easily aggregated in a suspension, the aggregation can be effectively suppressed because a trehalose is contained in the suspension of the present invention. As used herein, the "adherent" cell means a scaffold-dependent cell capable of surviving, proliferating, and producing substances by adhering to the scaffold. Examples of the adherent stem cell can include a pluripotent stem cell, a mesenchymal stem cell, a neural stem cell, a myeloid stem cell, and a germ stem cell. The adherent stem cell is preferably a mesenchymal stem cell or a pluripotent stem cell.

The mammalian cell may be a cell separated from a living body or a cell subcultured in vitro. The mammalian cells (population) contained in the mammalian cell suspension of the present invention are preferably those isolated or purified. As used herein, the "isolated or purified" means that the operation of removing components other than a desired component has been applied. The purity of the isolated or purified mammalian cells (the percentage of desired cells, such as the number of mammalian stem cells relative to the number of all cells) is typically 30% or more, preferably 50% or more, more preferably 70% or more, still more preferably 90% or more (for example, 100%).

The mammalian cells (population) contained in the suspension of the present invention preferably comprise the mammalian cells in a single cell state. As used herein, the "single cell state" means that cells do not get together to form a mass (in other words, an unaggregated state). The mammalian cells in a single cell state can be prepared by subjecting mammalian cells cultured in vitro to enzyme treatment with trypsin/EDTA or the like. The percentage of the mammalian cells in a single cell state in the mammalian cells is typically 70% or more, preferably 90% or more, more preferably 95% or more, still more preferably 99% or more (for example, 100%). The percentage of the cells in a single cell state can be determined by dispersing the mammalian cells in PBS, observing the dispersion under a microscope, and examining a plurality of (e.g., 1000) randomly selected cells for the presence of aggregation.

The mammalian cells are preferably floating in the suspension of the present invention. As used herein, the "floating" refers to that cells are held in a suspension without contacting with the inner wall of a container housing the suspension.

Examples of trehalose in the trehaloses used in the present invention can include α,β-trehalose as a disaccharide in which α-glucose and β-glucose molecules are 1,1-glycoside-linked and β,β-trehalose in which two β-glucose molecules are 1,1-glycoside-linked, in addition to α,α-trehalose as a disaccharide in which two α-glucose molecules are 1,1-glycoside-linked; among others, α,α-trehalose is preferable. These trehaloses can be produced by any well-known method such as chemical synthesis, production by a microorganism, and production by an enzyme; however, commercially available ones can also be used. Examples thereof can include α,α-Trehalose (from Hayashibara Shoji Co., Ltd.) and α,α-Trehalose (from Wako Pure Chemical Industries Ltd.).

The trehalose derivative in the trehaloses used in the present invention is not particularly limited provided that it is a glycosyltrehalose in which one or more sugar units are linked to trehalose as a disaccharide; glycosyltrehaloses include glucosyltrehalose, maltosyltrehalose, and maltotriosyltrehalose.

Examples of the salt of trehalose or its derivative in the trehaloses used in the present invention can include acid addition salts such as hydrochlorides, hydrobromates, hydroiodides, phosphates, nitrates, sulfates, acetates, propionates, toluenesulfonates, succinates, oxalates, lactates, tartrates, glycolates, methanesulfonates, butyrates, valerates, citrates, fumarates, maleates, and malates; metal salts such as sodium salts, potassium salts, and calcium salts; and ammonium salts and alkylammonium salts. These salts are each used in the form of a solution at the time of use, and their action preferably has the same potency as that of trehalose. These salts may form hydrates or solvates, and may be used alone or in a proper combination of 2 or more thereof.

The concentration of a trehalose applied to the mammalian cell suspension and the preventive agent against pulmonary embolism formation according to the present invention may be a concentration capable of preventing pulmonary embolism formation by cells such as stem cells, and can be properly selected depending on the number and concentration of suspended cells; however, preferred is a concentration sufficient for suppressing the aggregation and survival rate reduction of mammalian cells. A higher concentration of a trehalose increases the effect of preventing pulmonary embolism formation as well as the effect of suppressing the aggregation and survival rate reduction; however, an excessively high concentration of a trehalose has a possibility of adversely affecting the survival rate of cells. For example, the concentration of a trehalose applied to the mammalian cell suspension and the preventive agent against pulmonary embolism formation according to the present invention is typically 0.1% or more, preferably 0.5% or more, more preferably 1.0% or more, and typically 20% or less, preferably 15% or less, more preferably 5.0% or less in view of avoiding the adverse effect on the survival rate of stem cells. Thus, the concentration of a trehalose in the suspension is 0.1 to 20%, preferably 0.5 to 15%, more preferably 1.0 to 5.0%.

In the present invention, the "pulmonary embolism formation" in administration through a blood vessel means that intraarterially or intravenously transplanted (administered) mammalian cells form a state of clogging the peripheral arterial system of the lung, for example, one or more capillary blood vessels of the pulmonary artery. The "state of clogging" the peripheral arterial system of the lung does not necessarily require the stop of the cells in the peripheral arterial system of the lung, and only requires the obstruction of blood flow at the point in hand. The blood flow here does not have to stop completely, and is sufficient if a reduction in blood flow occurs to an extent of causing a reduced pulmonary function in a broad sense. The "pulmonary function" primarily means the uptake of oxygen from the air into the blood; however, it also encompasses the excretion of carbon dioxide and other gasses. The occurrence of pulmonary embolism formation by cells reduces blood flow in capillary blood vessels of a pulmonary artery, and causes tachypnea (increased breathing rate) and tachycardia (increased heart rate), increases blood pressure, such as pulmonary arterial pressure, or decreases blood oxygen partial pressure. Thus, the prevention of pulmonary embolism formation due to cell transplantation can reduce risks, such as tachypnea, tachycardia, increased blood pressure, and decreased blood oxygen partial pressure, due to the pulmonary embolism. In some cases, pulmonary embolism formation due to cell transplantation results in the development of pulmonary embolic diseases, such as a reduction in pulmonary function and a reduction in cardiac function (such as a function of moving blood into the inside of arteries or a cardiac function of moving blood to the outside of veins). In addition, the pulmonary embolism formation according to the present invention also encompasses a case where mammalian cells form a state of clogging the peripheral arterial system of the lung as well as other blood vessels.

In the mammalian cell suspension of the present invention, mammalian cells are typically suspended in a physiological aqueous solution comprising a trehalose as an active ingredient. On the other hand, the preventive agent against pulmonary embolism formation according to the present invention is roughly classified into a liquid form and a non-liquid form. The liquid form preventive agent is typically composed in the form of a physiological aqueous solution comprising a trehalose as an active ingredient, and mammalian cells can be suspended in the liquid form preventive agent to prepare a mammalian cell suspension of the present invention. The non-liquid type preventive agent is typically composed in the form of a material containing a trehalose, such as powder, to be added to a physiological aqueous solution in which mammalian cells are suspended, and the non-liquid type preventive agent can be added to the physiological aqueous solution in which mammalian cells are suspended to prepare a mammalian cell suspension of the present invention.

In addition, different aspects of the mammalian cell suspension of the present invention can include a method for preventing pulmonary embolism formation in the transplantation of cells, such as stem cells, in which a mammalian cell suspension comprising mammalian cells and a trehalose is administered through a blood vessel, and different aspects of the preventive agent against pulmonary embolism formation according to the present invention can include use of a trehalose in the preparation of a preventive agent against pulmonary embolism formation during administration of mammalian cells through a blood vessel.

Examples of the physiological aqueous solution can include physiological saline solution, phosphate buffered physiological saline solution, Tris buffered physiological saline solution, HEPES buffered physiological saline solution, Ringer's solutions (lactate Ringer's solution, acetate Ringer's solution, bicarbonate Ringer's solution, and the like), 5% glucose aqueous solution, liquid media for mammal culture, and isotonic aqueous solutions such as aqueous solutions of isotonic agents (glucose, D-sorbitol, D-mannitol, lactose, sodium chloride, and the like); among others, preferred is a Ringer's solution, more preferably lactate Ringer's solution, acetate Ringer's solution, or bicarbonate Ringer's solution, still more preferably lactate Ringer's solution. As used herein, the "isotonic" means having an osmotic pressure ranging from 250 to 380 mOsm/l. The physiological aqueous solution may further contain a stabilizer (e.g., human serum albumin or polyethylene glycol), a buffer (e.g., phosphate buffer or sodium acetate buffer), a chelating agent (e.g., EDTA, EGTA, citric acid, or salicylate), a solubilizer, a preservative, an antioxidant, and the like.

A trehalose may be used in combination with a dextran, which has been demonstrated to have a preventive effect against pulmonary embolism formation like the trehalose by the present inventors. In place of a trehalose or together with a trehalose may also be used maltose, glucose, sucrose, lactose, allose, galactose, sorbitol, xylitol, dextrin, cyclodextrin, or the like, which can be expected to have a preventive effect against pulmonary embolism formation like the trehalose.

The cells, such as stem cells, contained in the cell suspension of the present invention are present in a floating state, and cells in a floating state generally easily aggregate; however, the effect of a trehalose of the present invention suppresses cell aggregation and can maintain a single cell state for a long period of time.

The suspension of mammalian cells in a physiological aqueous solution containing a trehalose can be carried out by a method well-known in the art, such as pipetting or tapping. The temperature of the mammalian cell suspension of the present invention is typically in the range of 0 to 37° C., preferably 0 to 25° C. The density of mammalian cells in the suspension of the present invention may be a density capable of preventing pulmonary embolism formation by cells such as stem cells; however, it is preferably a density at which the effect of suppressing the aggregation of mammalian cells and a reduction in the survival rate thereof by a trehalose is achieved, and is typically in the range of $10^3$ to $10^{10}$ cells/ml.

The mammalian cell suspension of the present invention suppresses the aggregation of mammalian cells by a trehalose; thus, cell transplantation can be carried out using this to reduce the risk that a cannula is clogged with a cell aggregate. The mammalian cell suspension of the present invention suppresses a reduction in the survival rate of mammalian cells in the suspension by a trehalose; thus, the use of the suspension of the present invention permits cell transplantation using cells in a better state and can be expected to result in improving a therapeutic effect.

The mammalian cell suspension or the preventive agent against pulmonary embolism formation according to the present invention can be produced in the form of a mammalian cell suspension formulation or a preventive formulation against pulmonary embolism formation by housing in a suitable sterile container. Examples of the container can include bottles, vials, syringes, plastic bags such as an infusion solution bag, and test tubes. These containers can be formed from various materials such as glass and plastic. A cannula and/or an injection needle may be connected to the container for a mammalian cell suspension formulation so that the mammalian cell suspension of the present invention in the container can be infused into a patient.

The present invention will be more specifically described below with reference to Examples. However, these Examples are not intended to limit the technical scope of the present invention.

EXAMPLES

Example 1

1. Confirming that Solution for Stem Cell Suspension of Present Invention can be Used for Prevention of Pulmonary Embolism Formation by Stem Cells 1-1 Method 1-1-1 Preparation of MSC Suspension Used for Intravenous Administration to Rat

[1] MSC derived from the fat of female Lew/SsN Slc rats were detached by trypsin digestion treatment, followed by centrifugation at 200×g for 3 minutes to recover the cells.

[2] MSC was prepared at a concentration of $2 \times 10^6$ cells/ml by using Dulbecco's phosphate buffered saline (D-PBS) (from Invitrogen Co., Ltd.), followed by dispensing $1 \times 10^7$ cells (5 ml) into 3 tubes, to each of which 13 μl of 8.3 mg/ml XENOLIGHT DIR fluorescent reagent (from Caliper Co., Ltd., Product No. 125964) was added to label MSC at 37° C. for 30 minutes.

[3] After removing the labeling solution by centrifugation at 200×g for 3 minutes, 5 ml of D-PBS was added, and centrifugation was again performed at 200×g for 3 minutes to remove the supernatant. The precipitated cells were suspended to a MSC concentration of $2 \times 10^6$ cells/ml in a physiological saline solution ("Otsuka Normal Saline" from Otsuka Pharmaceutical Factory, Inc.), a lactate Ringer's solution ("LACTEC Injection" from Otsuka Pharmaceutical Factory, Inc.), and a 3% (30 mg/ml) trehalose (from Wako Pure Chemical Industries Ltd.)-containing lactate Ringer's solution to prepare an MSC-suspended physiological saline solution, an MSC-suspended lactate Ringer's solution, and an MSC-suspended trehalose-containing lactate Ringer's solution, respectively.

1-1-2 Intravenous Administration of MSC Suspension to Rat

[1] Female 10-week old Lew/SsN Slc rats were used. The rats were subjected to fasting 24 hours before administering each MSC suspension.

[2] To secure a route of administration to the rats, the rats were each restrained in a restrainer, and a 24G SURFLO indwelling needle was inserted into the tail vein.

[3] SOMNOPENTYL (50 mg/kg) (from Kyoritsu Seiyaku Corporation) was rapidly administered into the tail vein for anesthetic treatment. For maintenance anesthesia, 1 hour later 25 mg/kg of SOMNOPENTYL (from Kyoritsu Seiyaku Corporation) was additionally administered.

[4] To prevent blood coagulation, 100 IU/kg of heparin (from Mochida Pharmaceutical Co., Ltd.) was administered through a route of administration into the tail vein.

[5] The left carotid artery was exposed by cervical incision, and a polyvinyl chloride tube was inserted/fixed.

[6] The body temperature was held at 37° C. using a body temperature maintainer (a rectal temperature probe from Neuroscience, Inc. was inserted by 3.5 cm).

[7] Endotracheal intubation was performed using a 16G plastic indwelling needle, and the uninserted end of the indwelling needle was connected to a respirator for artificial breathing control (ventilation with air, ventilation amount: 10 ml/kg/stroke, and ventilation frequency: about 70 strokes/minute).

[8] To avoid the occurrence of spontaneous respiration, a muscle relaxant (2 or 4 mg/kg MIOBLOCK Intravenous Injection from MSD K.K.) was administered through a route of administration into the tail vein.

[9] To measure blood gas pressure (oxygen partial pressure $[pO_2]$ and carbon dioxide partial pressure) (mmHg) before administrating the MSC suspension, 300 μl of blood was collected through a carotid artery line.

[10] The 3 types of MSC suspensions prepared by the method described in the above "1-1-1 Preparation of MSC Suspension Used for Intravenous Administration to Rat" (MSC-suspended physiological saline solution, MSC-suspended lactate Ringer's solution, and MSC-suspended trehalose-containing lactate Ringer's solution) were each administered for 40 minutes to rats through the tail vein. Rat groups in which the MSC-suspended physiological saline solution, the MSC-suspended lactate Ringer's solution, and the MSC-suspended trehalose-containing lactate Ringer's solution were each intravenously administered were defined as an MSC-suspended physiological saline solution administration group (n=4), an MSC-suspended lactate Ringer's solution administration group (n=4), and an MSC-suspended trehalose-containing lactate Ringer's solution administration group (n=4), respectively.

1-1-3 Blood Oxygen Partial Pressure and MSC Image Analysis in Rat to Which MSC Suspension Was Administered

[1] Blood (300 μl) was collected through a carotid artery line every 10 minutes until 60 minutes after MSC suspension administration, and blood gas pressure (oxygen partial pressure $[pO_2]$ and carbon dioxide partial pressure) (mmHg) was measured using Chiron 348 (from Siemens AG).

As a control, the blood collected before the administration of the MSC suspensions prepared in the step [8] of the above "1-1-2 Intravenous Administration of MSC Suspension to Rat" was used.

[2] Bleeding was performed through the carotid artery after a lapse of 60 minutes from MSC suspension administration for euthanization.

[3] The lung was removed, and fluorescence and emission intensity were measured by image analysis using IVIS Spectrum (from Caliper Life Sciences Inc.) (excitation wavelength: 710 nm, absorption wavelength: 780 nm).

1-2 Result 1-2-1 Blood Oxygen Partial Pressure Analysis in Rat to Which MSC suspension Was Administered When the physiological saline solution and the lactate Ringer's solution were each used as an MSC-suspending solution, a reduction in blood oxygen partial pressure was observed from the start of MSC suspension administration, and the blood oxygen partial pressure was shown to be reduced at least until a point of time when 20 minutes had elapsed after the end of administration (60 minutes after administration) (FIG. 1, Table 1). On the other hand, when the trehalose-containing lactate Ringer's solution was used as an MSC-suspending solution, no reduction in blood oxygen partial pressure was observed during administration (0 to 40 minutes after the start of administration) and for at least 20 minutes after administration (40 to 60 minutes after the start of administration) (FIG. 1, Table 1). From these results, it is probable that whereas the administration (transplantation) of MSC suspended in the trehalose-free solution (the physiological saline solution or the lactate Ringer's solution) caused pulmonary embolism formation, the administration (transplantation) of MSC suspended in the trehalose-containing lactate Ringer's solution resulted in the prevention of pulmonary embolism formation.

TABLE 1

| Average | | 0 min | 10 min | 20 min | 30 min | 40 min | 50 min | 60 min |
|---|---|---|---|---|---|---|---|---|
| $pO_2$ | MSC-Suspended Physiological Saline Solution Administration Group | 1 | 0.827 | 0.804 | 0.785 | 0.790 | 0.825 | 0.901 |
| | MSC-Suspended Lactate Ringer's Solution Administration Group | 1 | 0.810 | 0.755 | 0.727 | 0.718 | 0.731 | 0.816 |
| | MSC-Suspended Trehalose-Containing Lactate Ringer's Solution Administration Group | 1 | 1.118 | 1.067 | 1.075 | 1.034 | 1.070 | 1.105 |

The blood oxygen partial pressures ($pO_2$) in the table are expressed as relative values when those in the blood collected before the administration of the MSC suspensions (0 minute) are each assumed as 1. Each value represents the average value of the results of 4 independent experiments.

1-2-2 Image Analysis of MSC in Rat to Which MSC Suspension Was Administered

When the biodistribution of MSC after the administration thereof to each rat living body was examined by image analysis, the use of the physiological saline solution as an MSC-suspending solution was shown to result in the highest amount of MSC-derived fluorescence in the lung (FIG. 2, Table 2). On the other hand, the use of the trehalose-containing lactate Ringer's solution as an MSC-suspending solution resulted in the lowest amount of MSC-derived fluorescence, and a statistically significant difference was observed compared to the use of the physiological saline solution ($p<0.05$ by Tukey's test) (FIG. 2, Table 2). These results show that whereas the administration (transplantation) of MSC suspended in the trehalose-free solution (the physiological saline solution or the lactate Ringer's solution) resulted in the accumulation of MSC in the lung, particularly capillary blood vessels of the lung, the administration (transplantation) of MSC suspended in the trehalose-containing solution (the lactate Ringer's solution) resulted in the reduced accumulation of MSC in the lung, particularly capillary blood vessels of the lung.

TABLE 2

| | Relative Total Radiation Efficiency (Saline = 100%) | Standard Deviation of Relative Total Radiation Efficiency (Saline = 100%) |
|---|---|---|
| MSC-Suspended Physiological Saline Solution Administration Group | 100.0% | 0.0% |
| MSC-Suspended Lactate Ringer's Solution Administration Group | 85.2% | 9.4% |
| MSC-Suspended Trehalose-Containing Lactate Ringer's Solution Administration Group | 62.1% | 8.0% |

Tukey's test: $p < 0.05$ (MSC-suspended physiological saline solution administration group vs MSC-suspended trehalose-containing lactate Ringer's solution administration group); $P = 0.1477$ (MSC-suspended lactate ringer's solution administration group vs MSC-suspended trehalose-containing lactate Ringer's solution administration group)
Each value in the table represents the average value of the results of 4 independent experiments.

From the above 2 results, it is probable that the transplantation of MSC using a trehalose-free solution results in pulmonary embolism formation by the accumulation of MSC in the lung, particularly capillary blood vessels of the lung, reduces the ability to uptake oxygen at the point in hand, and decreases blood oxygen partial pressure. On the other hand, it is probable that the transplantation of MSC using a trehalose-containing solution results in the suppression of MSC accumulation in the lung (pulmonary embolism formation), does not reduce the ability for the lung to uptake oxygen, and does not decrease blood oxygen partial pressure.

INDUSTRIAL APPLICABILITY

The present invention permits the prevention of pulmonary embolism formation in transplanting cells, such as stem cells (e.g., MSC), and the reduction of a risk of developing pulmonary embolic disease, and thus is useful in the field of medical transplantation in regenerative medicine or the like and the field of cancer treatment.

The invention claimed is:

1. A method for preventing pulmonary embolism formation in cell transplantation, comprising administering a mammalian cell suspension comprising mammalian cells and trehalose or its derivative, or salt thereof, and not comprising serum albumin, through a blood vessel.

2. The method according to claim 1, wherein the mammalian cells are mammalian stem cells.

3. The method according to claim 2, wherein the mammalian stem cells are mammalian mesenchymal stem cells or mammalian pluripotent stem cells.

4. The method according to claim 1, wherein the mammalian cells comprise the mammalian cells in a single cell state.

5. The method according to claim 1, wherein trehalose or its derivative, or a salt thereof has a concentration ranging from 0.1 to 20%.

6. The method according to claim 2, wherein the mammalian cells comprise the mammalian cells in a single cell state.

7. The method according to claim 3, wherein the mammalian cells comprise the mammalian cells in a single cell state.

8. The method according to claim 2, wherein trehalose or its derivative, or a salt thereof has a concentration ranging from 0.1 to 20%.

9. The method according to claim 3, wherein trehalose or its derivative, or a salt thereof has a concentration ranging from 0.1 to 20%.

10. The method according to claim 4, wherein trehalose or its derivative, or a salt thereof has a concentration ranging from 0.1 to 20%.

11. The method according to claim 6, wherein trehalose or its derivative, or a salt thereof has a concentration ranging from 0.1 to 20%.

12. The method according to claim 7, wherein trehalose or its derivative, or a salt thereof has a concentration ranging from 0.1 to 20%.

* * * * *